United States Patent [19]

Casey et al.

[11] Patent Number: 4,909,801

[45] Date of Patent: Mar. 20, 1990

[54] EYEDROP DISPENSER HAVING A BUMPER

[75] Inventors: William J. Casey; Paul Casey, both of Palm Beach Gardens, Fla.

[73] Assignee: Acorn Laboratories, Inc., Palm Beach Gardens, Fla.

[21] Appl. No.: 216,138

[22] Filed: Jul. 7, 1988

Related U.S. Application Data

[63] Continuation-in-part of Ser. No. 874,907, Jun. 16, 1986, abandoned.

[51] Int. Cl.[4] ............................................. A61M 35/00
[52] U.S. Cl. ..................................... 604/300; 222/210; D24/66
[58] Field of Search ................. 222/420, 421, 206–215, 222/420, 421, 422; 604/294–302; D23/14; D24/66

[56] References Cited

U.S. PATENT DOCUMENTS

| | | | |
|---|---|---|---|
| 2,669,232 | 2/1954 | Borowick | 604/298 |
| 2,673,661 | 3/1954 | Barton | 604/295 |
| 2,883,983 | 4/1959 | Biederman | 604/73 |
| 3,261,355 | 7/1966 | Burbig | 604/301 |
| 3,409,009 | 11/1968 | Vasse | 604/298 |
| 3,872,865 | 3/1975 | Casey | 604/302 |
| 3,945,381 | 3/1976 | Silver | 604/301 |
| 4,002,168 | 1/1977 | Petterson | 604/298 |
| 4,072,249 | 2/1978 | Ekenston et al. | 604/212 |
| 4,111,200 | 9/1978 | Sbarra et al. | 604/298 |
| 4,463,880 | 8/1984 | Kramer et al. | 222/420 |

FOREIGN PATENT DOCUMENTS

2142829  1/1985  United Kingdom ................. 604/295

Primary Examiner—Jerome L. Kruter
Attorney, Agent, or Firm—Nolte, Nolte and Hunter

[57] ABSTRACT

A generally egg-shaped eyedrop dispenser, with a nozzle provided on top of a squeezable hollow body. On top of the hollow body about the nozzle is a bumper having a smooth, generally dome-shaped, top surface substantially surrounding the nozzle. Both the body and bumper having a generally round shape when viewed from the top. The bumper reduces the consumer's fear of inadvertently jabbing his eye with the nozzle while applying eyedrops to his eye from the inverted dispenser. The bumper also makes it easier to apply eyedrops by allowing the consumer to rest the bumper on the bridge of his nose or on his brow while dispensing the eyedrops.

9 Claims, 8 Drawing Sheets

EYEDROP DISPENSER HAVING A BUMPER

This is a continuation-in-part of application Ser. No. 06/874,907, filed June 16, 1986 now abandoned.

BACKGROUND OF THE INVENTION

This invention relates to a dispenser with a pointed nozzle for applying a liquid eyedrop composition. This invention particularly relates to an improved bumper for an eyedrop dispenser which makes it easier to apply the eyedrops while reducing the user's fear of inadvertently jabbing the dispenser's nozzle in his eyes.

An eyedrop dispenser is well known from Casey U.S. Pat. No. 3,872,865 having a pointed nozzle surrounded by a dome-shaped bumper on top of a squeezable hollow body holding the eyedrops. The body and bumper of this patented dispenser have been provided with an oblong shape when viewed from the top, and the lower edge of the bumper has been press-fit, heat-sealed or otherwise permanently adhered to the midsection of the dispenser. The top of the bumper has been approximately coplanar with the tip of the nozzle, and an annular space has been provided between them so as not to interfere with the flow of eyedrops from the dispensing opening in the nozzle tip. When the dispenser has been inverted and held above the consumer's eye and then squeezed to apply eyedrops to the eye, the bumper has made the top of the dispenser appear generally blunt to the consumer's eye, despite the pointed tip of the dispenser's nozzle. As a result, the consumer has found it easier to apply an eyedrop composition, such as an aqueous solution of tetrahydrozoline hydrochloride, to his eye from the dispenser to relieve simple irritation of the eye. This is because the bumper has served to reduce the consumer's fear of inadvertently jabbing his eye with the tip of the dispenser's nozzle while administering eyedrops to the eye.

However, problems have been encountered in using the patented dispenser. In this regard, the construction described in U.S. Pat. No. 3,872,865 embodies a well surrounding the dropper tip and in which dirt may accumulate. Furthermore, the tip of the dispenser's nozzle has tended to wobble when the dispenser has been inverted and held over the consumer's eye and particularly when the dispenser has been squeezed to dispense eyedrops from its nozzle. This has made it difficult to get eyedrops to fall from the dispenser into the consumer's eye, without the eyedrops also falling all over the consumer's face. There has been a need, therefore, for an improved eyedrop dispenser, which makes it easier to get eyedrops into the consumer's eye and eliminates dirt accumulation problems.

SUMMARY OF THE INVENTION

In accordance with this invention, an improved eyedrop dispenser is provided which comprises:

a hollow body for holding a liquid eyedrop composition to be dispensed;

a nozzle on top of the body for dispensing its liquid contents; and a bumper on top of the body having a smooth, generally dome-shaped, top surface substantially surrounding the nozzle;

the bumper having a generally round shape when viewed from the top.

The bumper of this dispenser is sized so that, when inverted, it can rest on the bridge of the nose or on the brow of the consumer above his eye. This stabilizes the dispenser and substantially prevents its nozzle from wobbling, thereby making it easier to get the eyedrops to fall into the consumer's eye when the dispenser is squeezed. In several embodiments, the body and bumper are threadedly attached to one another where they both have a generally round, horizontal cross-section, so that the bumper can be removed from the body. In several embodiments, a cap for the nozzle coacts with the bumper to keep dirt and debris from accumulating on the external surfaces on top of the body of the dispenser not covered by the cap. In other embodiments, the bumper and nozzle are formed as a unit and both bumper and nozzle are covered by a cap when not in use.

DETAILED DESCRIPTION OF THE PREFERRED EMBODIMENTS

FIGS. 1–4 show one embodiment of the improved eyedrop dispenser of this invention, generally 10. The dispenser 10 comprises a squeezable hollow body 12 for holding eyedrops. The body 12 has a generally round shape when viewed from the top and has an integral hollow neck 14 on the top thereof with a screw thread 16 on its external surface. A conventional nozzle 18 is inserted in the open top of the neck 14. The nozzle 18 is adapted to dispense, in a dropwise manner, eyedrops from the dispenser body 12 through an opening 20 in the pointed tip 22 of the nozzle when the dispenser body is inverted.

Figure 1:
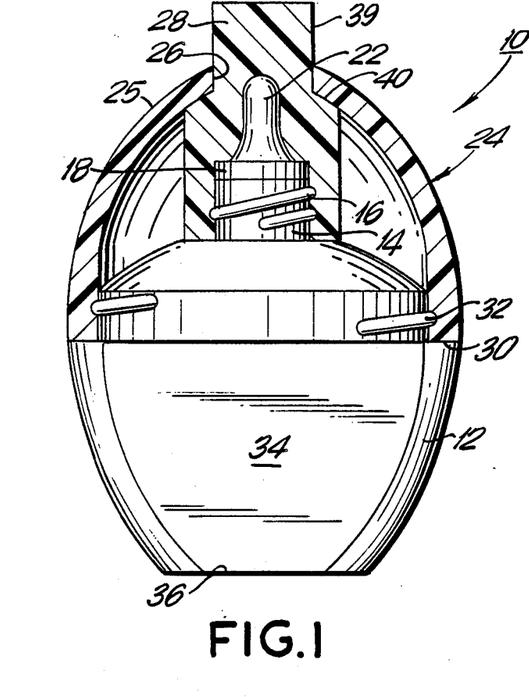
FIG. 1 is a schematic front elevation view of a first embodiment of the eyedrop dispenser of this invention. A bumper and a cap for the nozzle on top of the hollow body of the dispenser are shown in section, taken along the vertical center line of the dispenser.

Surrounding the top of the body 12 and its neck 14 and nozzle 18 is a bumper, generally 24, with a generally round shape when viewed from the top. The bumper 24 has an inverted cup-like configuration with a smooth, generally dome-shaped or concave downward, top surface 25. In the top of the bumper 24 is a generally circular, horizontal central opening 26 that is generally coplanar with the opening 20 in the tip 22 of the nozzle 18. The central opening 26 in the top of the bumper 24 defines an inner, generally cylindrical surface that substantially surrounds horizontally the tip 22 of the nozzle 18. As shown in FIG. 3, the bumper 24 and its central opening 26 and the tip 22 of the nozzle 18 and its opening 20 are preferably symmetrical about a common vertical axis which is also the vertical axis of the dispenser 10 and its hollow body 12. Preferably, the central opening 26 in the bumper 24 is also wide enough to accommodate the top portions of a generally cylindrical cap 28 which screws down onto the thread 16 on the neck 14 to seal the nozzle 18. A marginal bottom portion of the bumper 24, that is adjacent to its bottom edge 30 and has a generally round, horizontal cross section as shown in FIG. 3, is adapted to be screwed down onto a screw thread 32 on the external surface of the body 12, about its generally round midsection, to hold the bumper 24 securely on top of the dispenser 10. As seen from FIGS. 2 and 3, the dispenser 10, without its cap 28, has a generally egg-shaped appearance.

In accordance with this invention, the size and configuration of the body 12, nozzle 18, bumper 24 and cap 28 of the dispenser 10 are not critical, so long as they form a neat fluid-sealable package. The bumper 24, nozzle 18 and cap 28 are preferably made from a rigid plastic. In order to facilitate the dropwise dispensing of liquid out of the body 12 through the nozzle tip 22, it is preferred that the body 12 be made of a plastic which is flexible enough to allow the consumer to squeeze easily the body 12 inwardly. In this regard, it is also preferred that the bottom portions of the body 12 be provided with opposed, substantially flat, upstanding, indented surfaces 34 which make it easier for the user of the dispenser to grasp and squeeze the bottom portions of the body 12 to dispense fluid therefrom. Such indented surfaces 34 preferably extend vertically upward from a straight bottom edge 36 which terminates at a flat bottom surface 38 of the body 12.

As shown in FIG. 1, when the cap 28 has been screwed down onto the thread 16 on the neck 14, the nozzle 18, the bumper 24 can be screwed down onto the thread 32 on the body 12, so that: (a) the central opening 26 in the bumper 24 closely surrounds an upstanding cylindrical external surface 39 on the upper portions of the cap 28; and (b) a portion of the downwardly facing, interior surface of the bumper, about its central opening 26, sits on top of an annular, generally horizontal, external ledge 40 below the cylindrical external surface 39 of the cap 28. This prevents solid and liquid dirt and debris from accumulating on top of the body 12 about the cap 28 and nozzle 18 (e.g., when the dispenser 10 is being stored).

Figure 2:
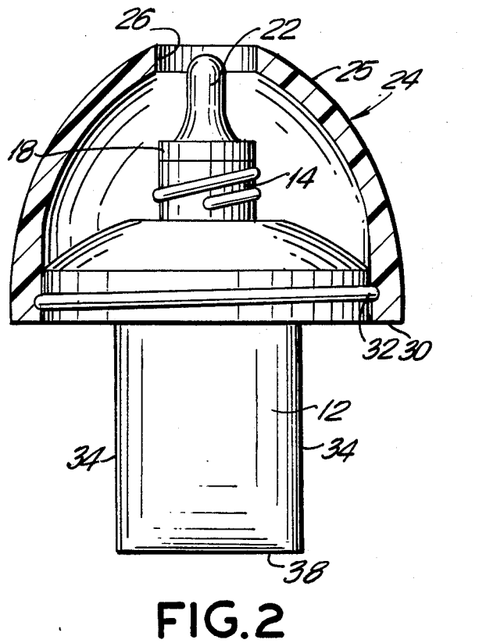
FIG. 2 is a schematic side elevation view of the dispenser of FIG. 1 with its cap removed. The bumper is shown in section, taken along the vertical center line of the dispenser.
Figure 3:
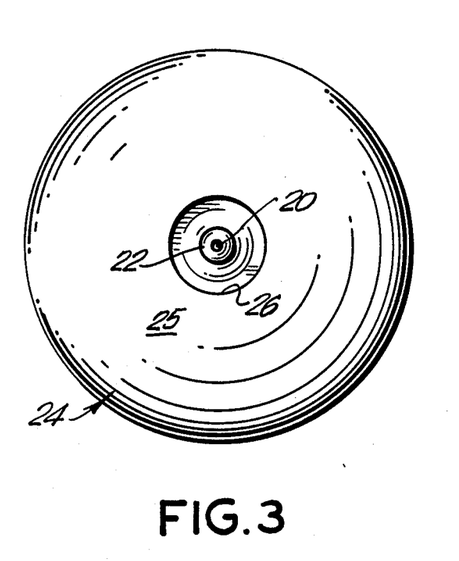
FIG. 3 is a schematic top plan view of the first embodiment of the dispenser as shown in FIG. 2.
Figure 4:
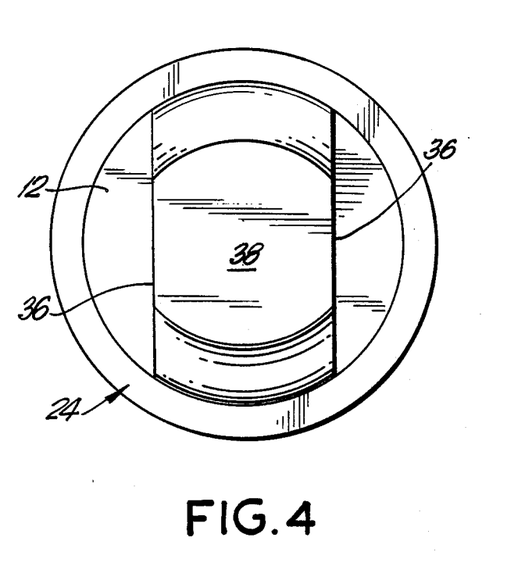
FIG. 4 is a schematic bottom plan view of the first embodiment of the dispenser as shown in FIG. 2.

When the dispenser 10 is to be used by the consumer; its bumper 24 can be screwed off its body 12; its cap 28 can be screwed off its neck 14; its bumper 24 can be screwed back on its body 12; its body 12, as shown in FIG. 2, can be inverted, and the top surfaces 25 of its bumper 24 can be rested on the bridge of the nose or on the brow of the consumer above his eye; and then, its pinched-in surfaces 34 can be squeezed together to dispense eyedrops from the tip 22 of its nozzle 18 into the consumer's eye. While eyedrops are being dispensed in this way from the inverted dispenser 10: (a) the bumper 24 reduces the consumer's fear of inadvertently jabbing his eye with the nozzle tip 22; and (b) the bumper 24, as supported on the bridge of the consumer's nose or on his brow, prevents the nozzle tip from wobbling appreciably so that the eyedrops can be accurately administered into the consumer's eye. To reclose the dispenser 10, its bumper 24 can be screwed off its body 12; its cap 28 can be screwed back on its neck 14 over its nozzle 18; and then its bumper 24 can be screwed back on its body 12 over its cap 28 as shown in FIG. 1.

Figure 5:
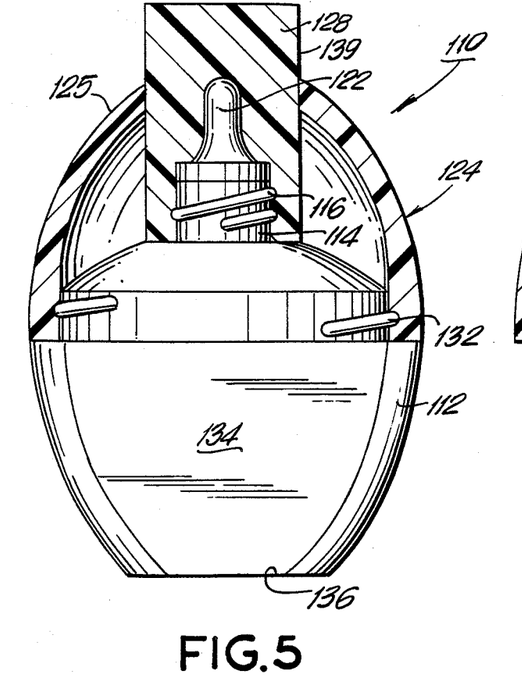
FIG. 5 is a schematic front elevation view of a second embodiment of the eyedrop dispenser of this invention. A bumper and a cap for the nozzle of the dispenser are shown in section, taken along the vertical center line of the dispenser.
Figure 6:
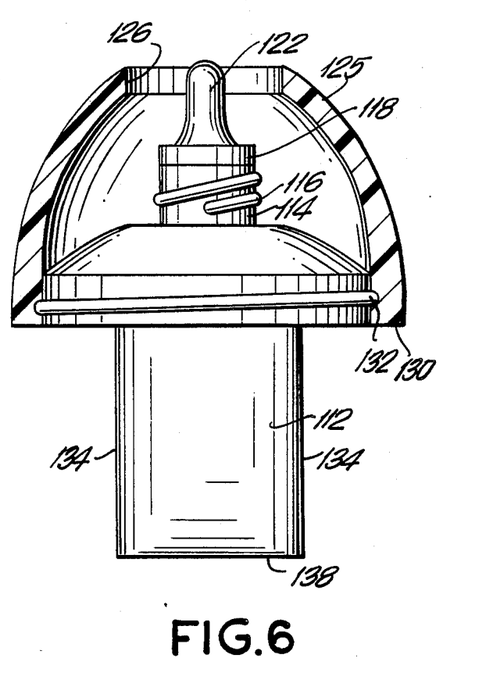
FIG. 6 is a schematic side elevation view of the dispenser of FIG. 5 with its cap removed. The bumper of the dispenser is shown in section, taken along the vertical center line of the dispenser.
Figure 7:
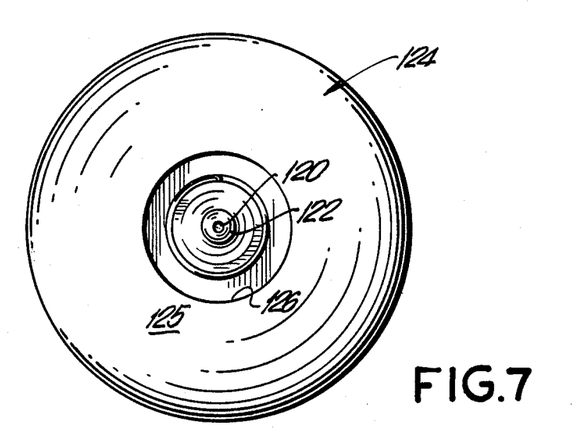
FIG. 7 is a schematic top plan view of the second embodiment of the dispenser as shown in FIG. 6.

FIGS. 5–7 show a second embodiment of the eyedrop dispenser of this invention, generally 110, with elements having reference numerals which differ by 100 from the corresponding elements of the dispenser 10 of FIGS. 1–4. The dispenser 110 has a squeezable hollow body 112 which is identical to the body 12 of the dispenser 10 of FIGS. 1–4, including an integral hollow neck 114 having a screw thread 116 on its external surface and a nozzle 118, with an opening 120 in its point tip 122, that is inserted in the open top of the neck 114. A bumper 124 on top of the body 112 of the dispenser 110 has an inverted cup-like configuration with a smooth, generally dome-shaped top surface 125. Preferably, a central opening 126 in the top of the bumper 124 defines an inner, generally cylindrical surface which substantially surrounds horizontally the tip 122 of the nozzle 118, including the opening 120 therein, and can accommodate the top portions of a cap 128 which screws down onto the threaded neck 114 to seal the nozzle 118. In this regard, the bumper 124 and cap 128 differ from the bumper 24 and cap 28 of the dispenser 10 of FIGS. 1–4 only in that the cap 128 does not have an annular, generally horizontal, external ledge and the bumper 124 is not adapted to sit on such a ledge. A generally round, marginal bottom portion of the bumper 124 can be screwed down onto a thread 132 on the generally round midsection of the body 112 so that, when the nozzle 118 is capped, the central opening 126 in the bumper 124 closely surrounds an upstanding cylindrical surface 139 on the top portions of the cap 128 so as to prevent dirt or debris from accumulating on top of the body 112 about the nozzle 118 and cap 128 (e.g., when the dispenser 110 is being stored). As seen from FIGS. 6 and 7, the dispenser 110, without its cap 128, has a generally egg-shaped appearance.

Like the dispenser 10 of FIGS. 1–4, when the dispenser 110 of FIGS. 5–7 is to be used by the consumer: its bumper 124 can be screwed off its body 112; its cap 128 can be screwed off its neck 114; its bumper 124 can be screwed back on its body 112; its body 112, as shown in FIG. 6, can be inverted, and the top surface 125 of its bumper 124 can be rested on the bridge of the nose or on the brow of the consumer above his eye; and then, its pinched-in surfaces 134 can be squeezed together to dispense eyedrops from the opening 120 in the tip 122 of its nozzle 118 into the consumer's eye, accurately and without fear. Then, the dispenser 110 can be reclosed by screwing its bumper 124 off its body 112; screwing its cap 128 back on its neck 114 over its nozzle 118; and then screwing its bumper 124 back on, over its cap 128 as shown in FIG. 5.

Figure 8:
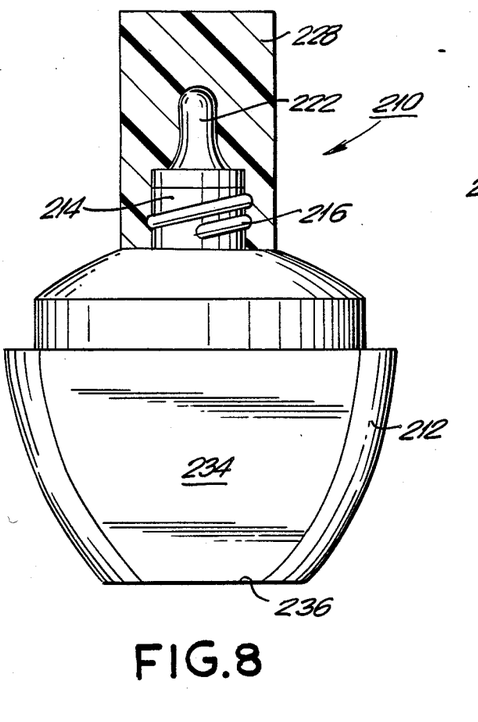
FIG. 8 is a schematic front elevation view of a third embodiment of the eyedrop dispenser of this invention. A cap on the nozzle of the dispenser is shown in section, taken along the vertical center line of the dispenser.
Figure 9:
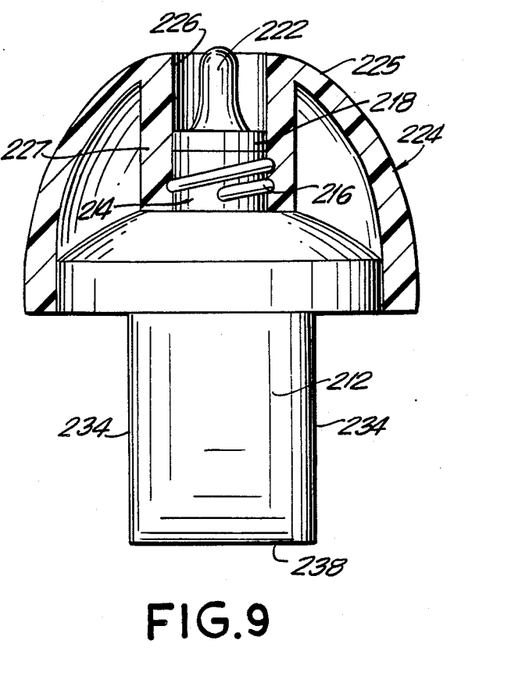
FIG. 9 is a schematic side elevation view of the dispenser of FIG. 8, with its cap replaced by a bumper for its nozzle. The bumper is shown in section, taken along the vertical center line of the dispenser.
Figure 10:
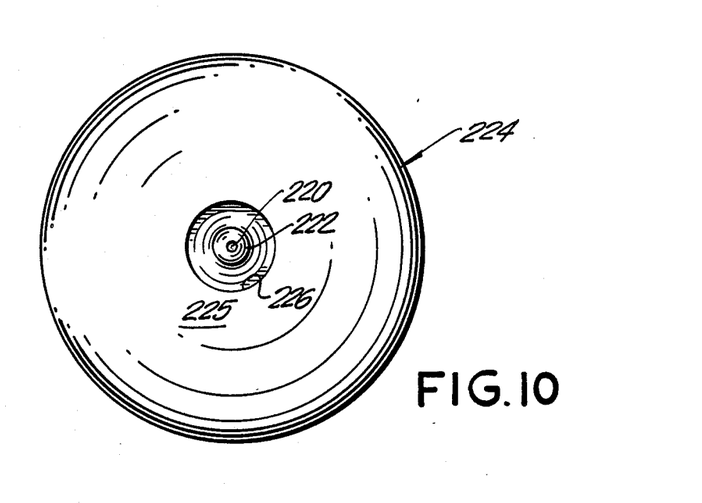
FIG. 10 is a schematic top plan view of the third embodiment of the dispenser as shown in FIG. 9.

Shown in FIGS. 8–10 is a third embodiment of the eyedrop dispenser of this invention, generally 210, with elements having reference numerals which differ by 100 from the corresponding elements of the dispenser 110 of FIGS. 5–7. The hollow body 212 of the dispenser 210 of FIGS. 8–10 is the same as the body 112 of the dispenser 110 of FIGS. 5–7 except the body 212 does not have a screw thread about its midsection. The cap 228 of the dispenser 210 is identical to the cap 128 of the dispenser 110 of FIGS. 5–7. The bumper 224 of the dispenser 210 is substantially the same as the bumper 124 of the dispenser 110 of FIGS. 5–7. However, the bumper 224 is not adapted to be screwed down onto a screw thread about the midsection of the body 212. Instead, the bumper 224 is provided with a substantially cylindrical, central member 227 that extends downwardly from the central opening 226 in the top of the bumper's smooth, generally dome-shaped, top surface 225 and that has its axis aligned wit the vertical axis of the central opening 226, so that the central member 227 can horizontally surround the neck 214 and nozzle 218 on the body 212 when the bumper 224 is mounted on top of the body 212. In this regard, the bottom portion of the central member 227 of the bumper 224 is adapted to be screwed down onto the screw thread 216 on the external surface of the neck 214 to hold the bumper 224 securely on top of the body 212 of the uncapped dispenser 210 and provide the uncapped dispenser with a generally egg-shaped appearance as shown in FIGS. 9 and 10.

When the dispenser 210 of FIGS. 8–10 is to be used by the consumer: its cap 228 can be screwed off the thread 216 on its neck 214; the central member 227 of its bumper 224 can be screwed on to the thread 216 on its neck 214 to hold the bumper on its body 212; its body 212, as shown in FIG. 9, can be inverted, and the top surface 225 of its bumper 224 can be rested on the bridge of the nose or on the brow of the consumer above his eye; and then, its pinched-in surfaces 234 can be squeezed together to dispense eyedrops from the opening 220 in the tip 222 of its nozzle 118 into the consumer's eye, accurately and without fear. Then, the dispenser 210 can be reclosed by screwing its bumper 224 off its neck 214 and then screwing its cap 228 back on its neck 214 over its nozzle 218 as shown in FIG. 8.

Figure 11:
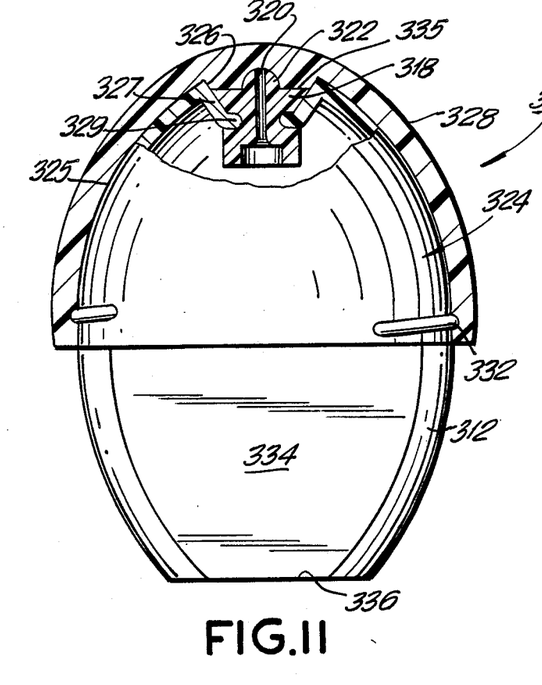
FIG. 11 is a schematic front elevation view of a fourth embodiment of the eyedrop dispenser of this invention. A bumper for the nozzle of the dispenser is incorporated into the top portions of the hollow body of the dispenser. The front top portions of the bumper and body and the front portions of the nozzle are cut away so as to show the nozzle in section, taken along the vertical center line of the dispenser.
Figure 12:
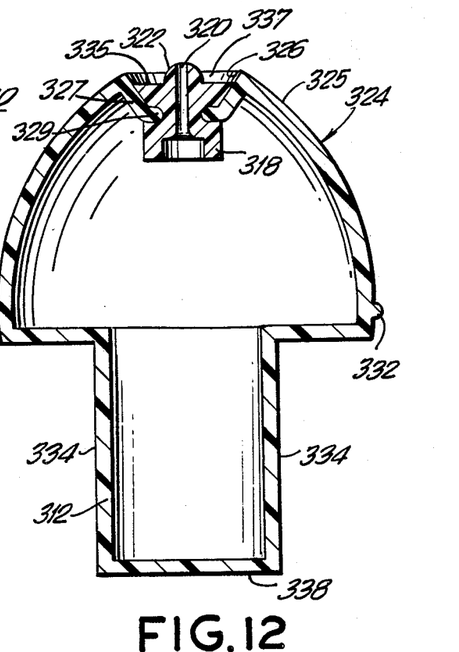
FIG. 12 is a schematic side view of the dispenser of FIG. 11, taken in section along the vertical center line of the dispenser, with its cap removed.
Figure 13:
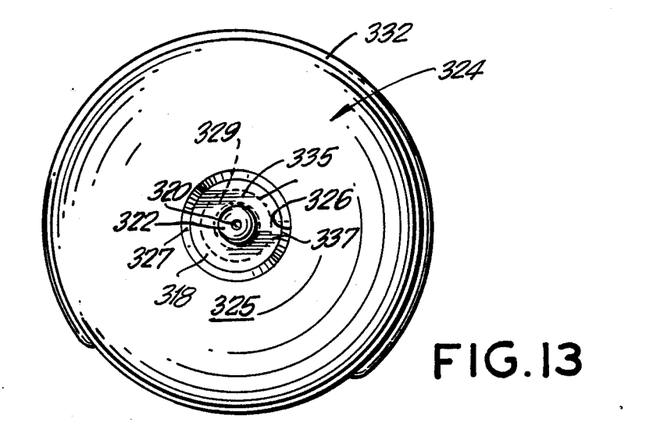
FIG. 13 is a schematic top plan view of the fourth embodiment of the dispenser as shown in FIG. 12.

Shown in FIGS. 11–13 is a fourth embodiment of the eyedrop dispenser of this invention, generally 310, with elements having reference numerals which differ by 300 from the corresponding elements of the dispenser 10 of FIGS. 1–4. The dispenser 310 of FIGS. 11–13 has a squeezable hollow body 312 with a generally round shape when viewed from the top. On the top of the body 312 and integral with it is a bumper 324 with a generally round shape when viewed from the top. The bumper 324 has a smooth, generally dome-shaped top surface 325 and a generally circular, central opening 326 in the top thereof. The bumper 324 has a conical central member 327 that extends downwardly from its central opening 326 and converges toward a common vertical axis with the bumper 324, central opening 326 and body 312. The bottom of the central member 327 is provided with an annular bead 329 which mates with, and holds, a nozzle 318 inserted in the top of the body 312 and bumper 324. The opening 320 in the tip 322 of the nozzle 318 is substantially surrounded horizontally by the central opening 326 in the top of the bumper 324, and the tip 322 of the nozzle 318 has a substantially flat, annular surface 335 surrounding it which lies below the central opening 326 in the bumper 324 so as to form, with the central member 327, a small well 338 about the nozzle tip. A screw thread 332 is provided on the external surface of the body 312 about its midsection. A dome-shaped cap 328, that is generally round when viewed from the top, can be screwed down onto the screw thread 332 to cover the top surface 325 and the central opening 326 of the bumper 324 so as to seal the nozzle 318 and the well 337 and prevent dirt and debris from accumulating on the external surfaces on top of the body 312 and the bumper 324 and on the nozzle 318 and in the well 337. As seen from FIGS. 11–13, the dispenser 310, with or without its cap 328, has a generally egg-shaped appearance.

When the dispenser 310 of FIGS. 11–13 is to be used by the consumer: its cap 328 can be screwed off its body 312; its body 312, as shown in FIG. 12, can be inverted, and the top surface 325 of its bumper 324 can be rested on the bridge of the nose or on the brow of the consumer above his eye; and then, its pinched-in surfaces 334 can be squeezed together to dispense eyedrops from the tip 322 of its nozzle 318 into the consumer's eye, accurately and without fear. Then, the dispenser 310 can be reclosed by simply screwing its cap 328 back on its body 312 over its bumper 324 and its nozzle 318 as shown in FIG. 11.

Shown in FIGS. 14–19 is a fifth embodiment of the eyedrop dispenser of this invention, generally 410, with elements having reference numerals which differ by 400 from the corresponding elements of the dispenser 10 of FIGS. 1–4. The hollow body 412 and integral bumper 424 of the dispenser 410 of FIGS. 14–19 are identical to the integral body 312 and bumper 324 of the dispenser 310 of FIGS. 11–13. The nozzle 418 of the dispenser 410 is substantially the same as the nozzle 318 of the dispenser 310 of FIGS. 11–13. The nozzle tip 422 extends somewhat above the central opening 426 in the top of the bumper 424, but in use, the nozzle tip appears to the consumer to be approximately coplanar with the top of the bumper 424. The nozzle tip 422 has a concave downward, annular surface 436 surrounding it. The annular surface 435 has substantially the same curvature as the top surface 425 of the bumper 424 and lies within, not below, the central opening 426 in the bumper 424. As a result, there is substantially no well formed about the nozzle tip 422. As with the dispenser 310 of FIGS. 11–13, the dispenser 410 of FIGS. 14–19 has a screw thread 432 on the external surface of its hollow body 412 about its midsection, and a dome-shaped cap 428, that is generally round when viewed from the top, can be screwed down onto the screw thread 432 to cover the top surface 425 of the bumper 424 and the nozzle 418 so as to seal the nozzle and prevent dirt and debris from accumulating on the external surfaces on top of the body 412 and bumper 424. As seen from FIGS. 14–19, the dispenser 410, with or without its cap 428, has a generally egg-shaped appearance.

Figure 14:
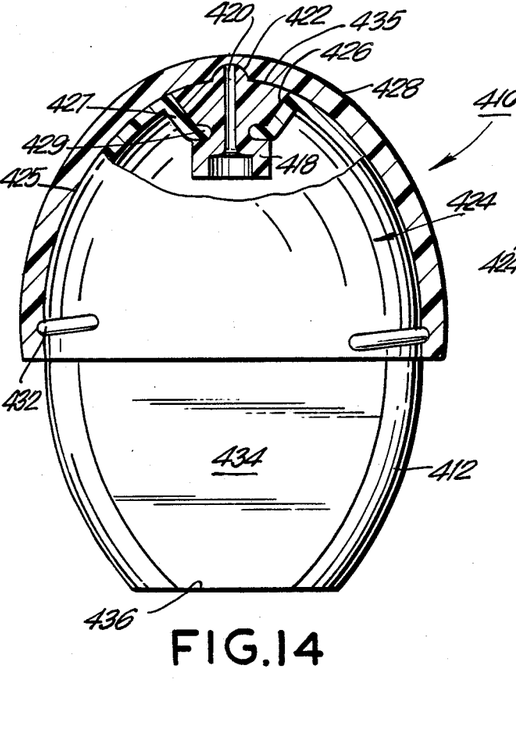
FIG. 14 is a schematic front elevation view of a fifth embodiment of the eyedrop dispenser of this invention. A bumper for the nozzle of the dispenser is incorporated into the top portions of the hollow body of the dispenser. The front top portions of the bumper and body and the front portions of the nozzle are cut away so as to show the nozzle in section, taken along the vertical center line of the dispenser. A cap for the nozzle is also shown in section, taken along the vertical center line of the dispenser.
Figure 15:
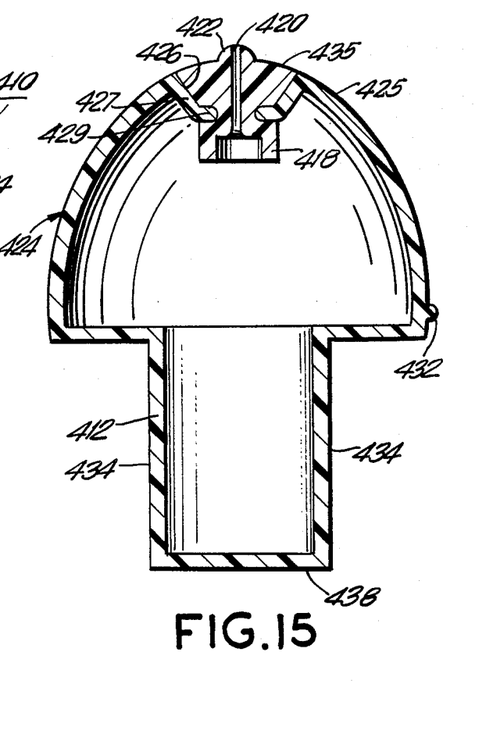
FIG. 15 is a schematic side view of the dispenser of FIG. 14, taken in section along the vertical center line of the dispenser, with its cap removed.
Figure 16:
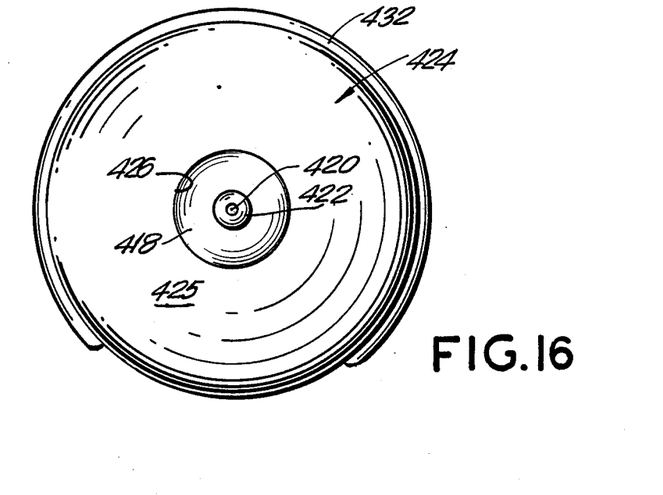
FIG. 16 is a schematic top plan view of the fifth embodiment of the dispenser as shown in FIG. 15.
Figure 17:
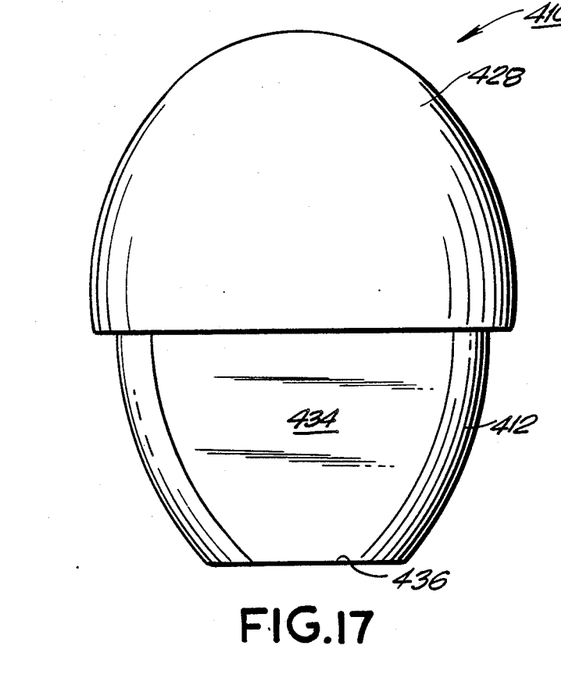
FIG. 17 is a schematic front elevation view of the fifth embodiment of the dispenser of FIG. 14.
Figure 18:
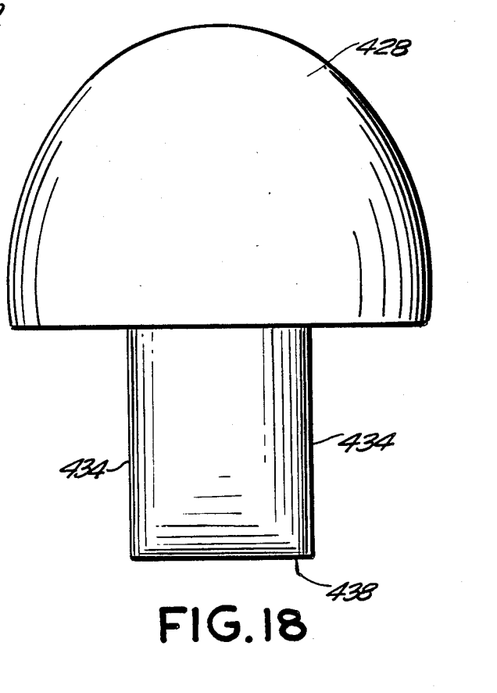
FIG. 18 is a schematic side elevation view of the fifth embodiment of the dispenser of FIG. 14.
Figure 19:
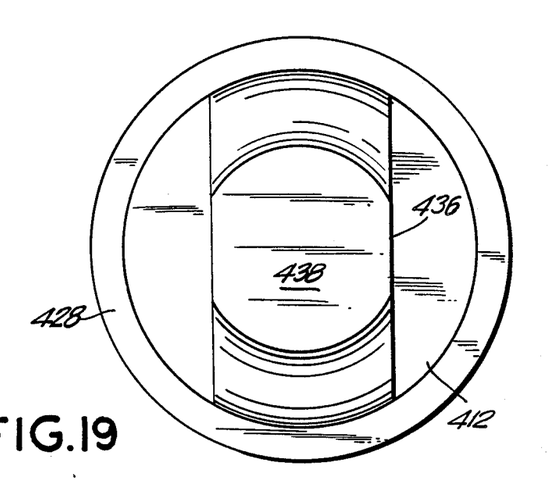
FIG. 19 is a schematic bottom plan view of the fifth embodiment of the dispenser of FIG. 14.

When the dispenser 410 of FIGS. 14–19 is to be used by the consumer; its cap 428 can be screwed off its body 412; its body 412, as shown in FIG. 15, can be inverted, and the top surface 425 of its bumper 424 can be rested on the bridge of the nose or on the brow of the consumer above his eye; and then, its pinched-in surfaces 434 can be squeezed together to dispense eyedrops from the tip 422 of its nozzle 418 into the consumer's eye, accurately and without fear. Then, the dispenser 410 can be reclosed by simply screwing its cap 428 back on its body 412 over its bumper 424 and its nozzle 418 as shown in FIGS. 14, 18 and 19.

Figures 20, 21, 22:
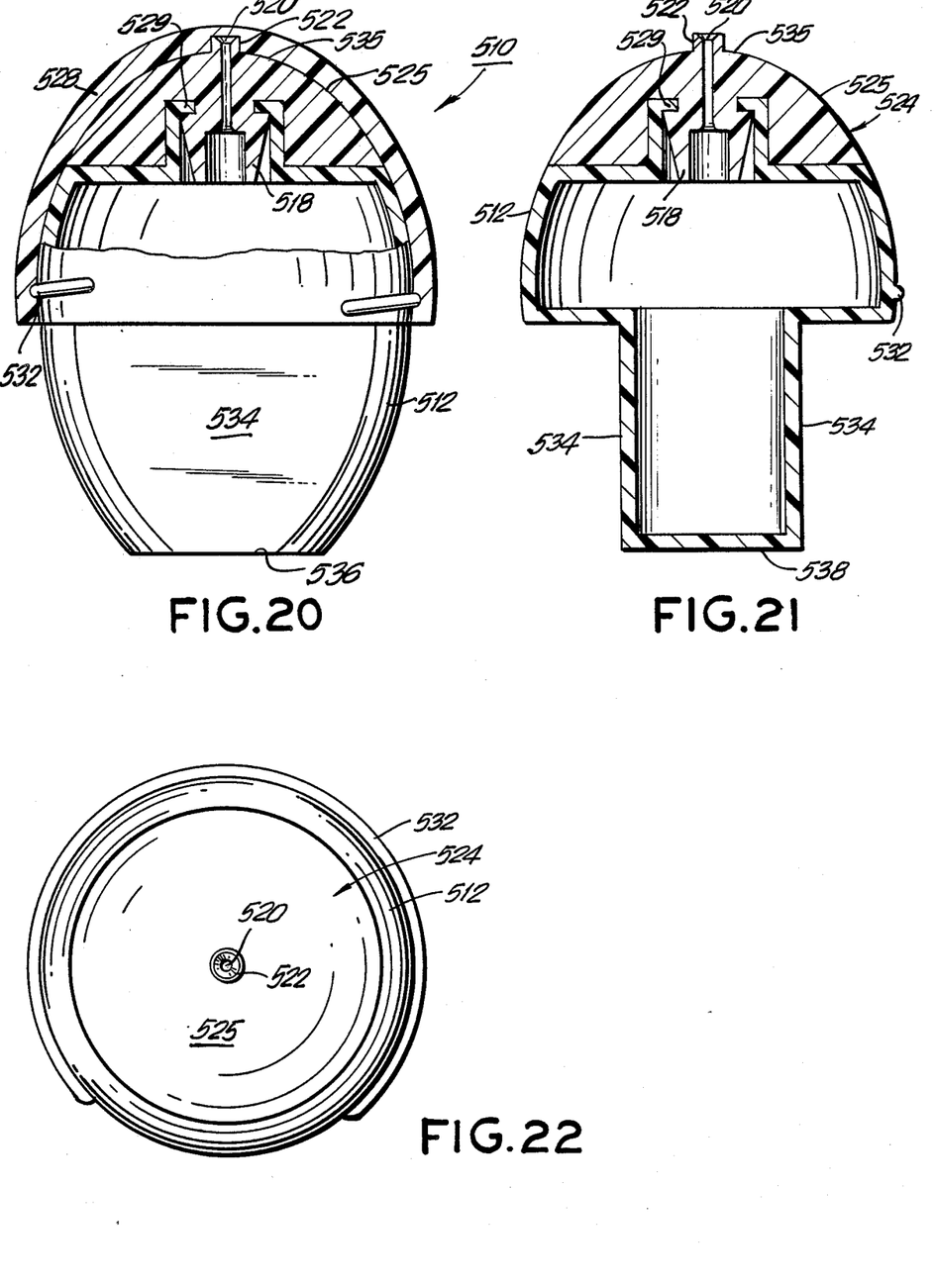
FIG. 20 is a schematic front elevation view of a sixth embodiment of the eyedrop dispenser of this invention. A bumper for the nozzle of the dispenser is incorporated into the nozzle and is located on top of the hollow body of the dispenser. The front top portions of the body and the front portions of the nozzle and bumper are cut away so as to show the nozzle and bumper in section, taken along the vertical center line of the dispenser. A cap for the nozzle is also shown in section, taken along the vertical center line of the dispenser.
FIG. 21 is a schematic side view of the dispenser of FIG. 20, taken in section along the vertical center line of the dispenser, with its cap removed.
FIG. 22 is a schematic top plan view of the sixth embodiment of the dispenser as shown in FIG. 21.
Figure 23:
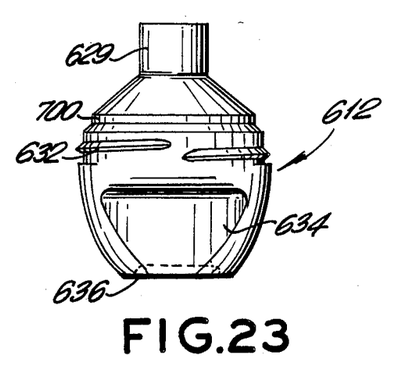
FIG. 23 is a schematic front elevational view of yet another embodiment of the eyedrop dispenser of the invention showing the hollow container portion.
Figure 24:
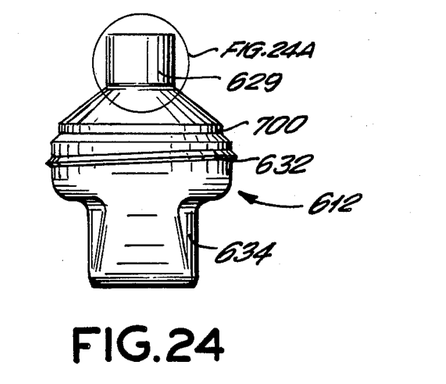
FIG. 24 is a schematic end view of the container portion of FIG. 23.
Figure 24A:
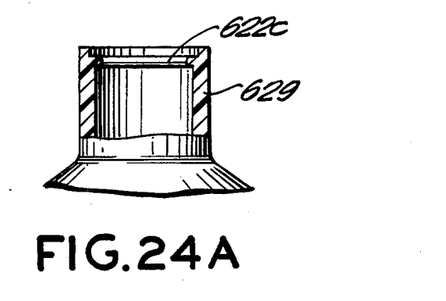
FIG. 24A is a schematic cross sectional view of the encircled detail of FIG. 23.
Figure 25:
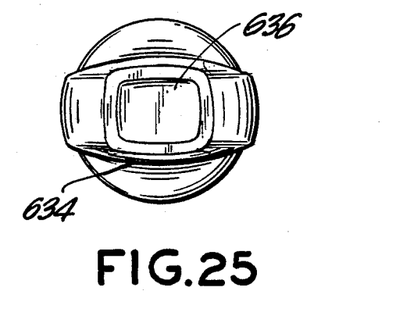
FIG. 25 is a schematic bottom view of the dispenser portion of FIG. 24.
Figure 26:
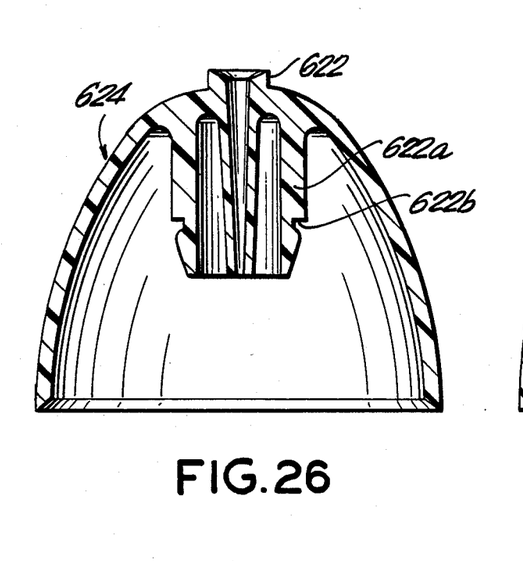
FIG. 26 is a schematic cross sectional view in larger scale of the integral nozzle and bumper portion of the dispenser of FIGS. 23–25.
Figure 27:
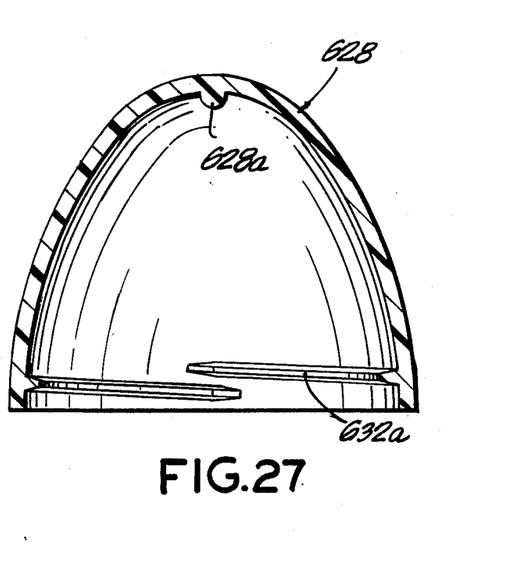
FIG. 27 is a schematic cross sectional view also in larger scale of the cap for the nozzle and bumper of the dispenser of FIGS. 23–26.

Shown in FIGS. 20–22 is a sixth embodiment of the eyedrop dispenser of this invention, generally 510, with elements having reference numerals which differ by 100 from the corresponding elements of the dispenser 410 of FIGS. 14–19. The dispenser 510 of FIGS. 20–22 has a squeezable hollow body 512 with a generally round shape when viewed from the top. On top of the body 512 is an annular bead 529 which mates with, and holds, a one-piece nozzle 518 and surrounding bumper 524 inserted in the top of the body 512. The one-piece nozzle 518 and bumper 524 overlie the body 512 and have a generally round shape when viewed from the top. The nozzle tip 522 extends somewhat above the top surface 525 of the bumper 524, and the concave downward, annular surface 535 surrounding the nozzle tip 522 has substantially the same curvature as the top surface 525 of the bumper 524 so there is not well formed about the nozzle tip 522. A screw thread 532 is provided on the external surface of the body 512 about is midsection, and a dome-shaped cap 528, that is generally round when viewed from the top, can be screwed down onto the screw thread 532 to cover the top surfaces 525 and 535 of the integral nozzle 518 and bumper 524 and cover the nozzle tip 522 so as to seal the nozzle and prevent dirt and debris from accumulating on the external surfaces on top of the one-piece nozzle and bumper. As seen from FIGS. 21 and 22, the dispenser 510, with or without its cap 528, has a generally egg-shaped appearance.

When the dispenser 510 of FIGS. 20–22 is to be used by the consumer: its cap 528 can be screwed off its body 512; its body 512, as shown in FIG. 21, can be inverted, and the top surface 525 of its bumper 524 can be rested on the bridge of the nose or the brow of the consumer above his eye; and then, its pinched-in surfaces 534 can be squeezed together to dispense eyedrops from the tip 522 of its nozzle 518 into the consumer's eye, accurately and without fear. Then, the dispenser 510 can re reclosed by simply screwing its cap 528 back on its body 512 over its one-piece nozzle and bumper as shown in FIG. 20.

In a preferred embodiment of FIGS. 23–27, the cap 628 is screwed onto and off the hollow body; i.e., the container portion 612, exposing the outside surface of the bumper 624 which in this instance is integral with the nozzle 622, the inner annular portion 622a of which fits within the neck 629 extending from the upper portion of the container portion 612. Circular indent 622b on the nozzle annular portion and circular detent 622c on the neck 629 mate for stability although indent and detent annular portions, not shown, may be provided for that purpose on the container body and bumper where they mate above the threads 632 around the outer peripheral portions of a shoulder 700 which extends to neck 629. The cap 628 and container body 612 provide mating threads 632 and 632a, respectively, for securing the cap to the container.

The cap fits about the bumper snugly and provides a stopper or plug 628a which fits into the concave mouth of the nozzle when the cap is screwed onto the body.

Flat bottom 636 is provided on the container for stabilizing the dispenser in the standing position. Indented sides 634 provide the surface for the fingers and thumb of the user to squeeze the dispenser when upside down with the dome 624 resting upon the outer regions of the eye socket.

It it is thought that this invention and many of its attendant advantages will be understood from the foregoing description, and it will be apparent that various changes and modifications can be made in the invention without departing from the spirit and scope thereof or sacrificing all of its material advantages, the dispenser 10, 110, 210, 310, 410 and 510 of FIGS. 1–22 being merely preferred embodiments. In this regard, terms such as "top", "bottom", "down", "above", "horizontal" and "vertical" are used simply as relative terms to describe the dispensers 10, 110, 210, 310, 410 and 510 as shown in FIGS. 1–22 and as claimed hereinafter.

We claim:

1. An eyedrop dispenser which comprises:
a wall structure defining a hollow body at its lower portion for holding liquid eyedrop composition to be dispensed, an upper portion of said wall structure having an egg-shaped exterior surface, a blunt end of which constitutes a top of said dispenser;
a nozzle in fluid communication with said hollow body for dispensing its liquid contents, said nozzle extending through said wall structure along an axis of symmetry of said egg-shaped exterior surface with a dispensing tip of said nozzle disposed centrally of said dispenser top;
said wall structure further defining at its lower portion wall surfaces contiguous with said top and indented along opposing wall surfaces symmetrically disposed on either side of said axis of symmetry, said opposing surfaces extending upwardly from a flat bottom surface and comprising means for holding said dispenser between the digits and thumb of the user's hand and constituting the sole means for squeezing said body to dispense dropwise therefrom the eyedrop solution contained in said body;
said egg-shaped exterior surface comprising bumper means of sufficient rigidity and size for resting stably and without wobble against the surface of the anatomical structures adjacent the eye of the user with the nozzle dispensing tip overlying the user's eye in all rotational positions of said dispenser about said axis of symmetry, while preventing contact between the user's eye and said dispensing tip; and
said egg-shaped exterior surface being contiguous with and extending continuously from said nozzle throughout 360° of its axis of symmetry so as to comprise means for averting any entrapment of debris in the region immediately surrounding said dispensing tip.

2. An eyedrop dispenser according to claim 1, wherein said dispensing tip of said nozzle projects slightly above said dispenser tip.

3. An eyedrop dispenser according to claim 1, wherein said egg-shaped exterior surface of said wall structure upper portion extends divergently from said dispenser top to a plane perpendicular to said axis of symmetry substantially midway between said dispenser top and said lower portion of said dispenser, the remaining said wall structure which defines said hollow body and which underlies said plane including said opposing wall surfaces comprising said holding and squeezing means, said holding and squeezing means comprising a spaced parallel pair of flat walls extending perpendicularly from said plane to the bottom of said lower portion and equidistantly from said axis of symmetry.

4. An eyedrop dispenser according to claim 3, wherein said wall structure upper portion having said egg-shaped exterior surface is an assembly of two sub-portions, one sub-portion having said nozzle disposed therein, the other sub-portion being of one-piece with said remaining wall structure defining said hollow body.

5. An eyedrop dispenser according to claim 3, further comprising a removable cap for covering said wall structure portion and sealing said nozzle at its dispensing tip, said cap being provided with a wall of substantially uniform thickness, the interior surface of which is complementary to said egg-shaped exterior surface of said wall structure portion to provide a close mating relationship therewith.

6. An eyedrop dispenser according to claim 1, wherein said hollow body comprises at its upper portion, a cylindrical annulus extending from a shoulder portion of said body, said nozzle comprises an inner channel extending and fitting into said annulus, said portion of said wall structure having an egg-shaped exterior being integral with said nozzle and extending continuously between said nozzle and the other peripheral portions of said shoulder portion so as to be contiguous with and a part of said wall structure defining a hollow body from said nozzle to said shoulder portion.

7. The eyedrop dispenser of claim 6, including means for securing said integral nozzle and egg-shaped wall structure to said hollow body.

8. The eyedrop dispenser of claim 7, wherein said securing means are indent and detent means on said integral nozzle and egg-shaped wall structure and on said hollow body.

9. An eyedrop dispenser which comprises:
a wall structure defining a hollow body at its lower portion for holding liquid eyedrop composition to be dispensed, an upper portion of said wall structure having an egg-shaped exterior surface, a blunt end of which constitutes a top of said dispenser;
a nozzle in fluid communication with said hollow body for dispensing its liquid contents, said nozzle extending through said wall structure along an axis of symmetry of said egg-shaped exterior surface with a dispensing tip of said nozzle disposed centrally of said dispenser top;
said wall structure further defining at its lower portion wall surfaces symmetrically disposed on either side of said axis of symmetry, said wall surfaces extending upwardly from a flat bottom surface and comprising means for holding said dispenser between the digits and thumb of the user's hand and constituting the sole means for squeezing said body to dispense dropwise therefrom the eyedrop solution contained in said body;
said egg-shaped exterior surface being convex, diverging toward said lower portion from said nozzle and constituting bumper means of sufficient rigidity and size for resting stably and without wobble against the surface of the anatomical structures adjacent the eye of the user with the nozzle dispensing tip overlying the user's eye in all rotational positions of said dispenser about said axis of symmetry, while preventing contact between the user's eye and said dispensing tip; and
said egg-shaped exterior surface being contiguous with and extending continuously from said nozzle through 360° of its axis of symmetry so as to comprise means for averting any entrapment of debris in the region immediately surrounding said dispenser tip.

* * * * *